United States Patent [19]

Gehrer et al.

[11] Patent Number: 5,714,430
[45] Date of Patent: Feb. 3, 1998

[54] MIXTURES CONTAINING FINE METALLIC SILVER PARTICLES ON A NEUTRAL TO BASIC NON-ZEOLITE CARRIER OXIDE

[75] Inventors: Eugen Gehrer, Ludwigshafen; Richard Thoma, Battenberg; Giorgio Greening, Rossdorf; John-Bryan Speakman, Bobenheim, all of Germany

[73] Assignee: BASF Aktiengesellschaft, Ludwigshafen, Germany

[21] Appl. No.: 499,828

[22] Filed: Jul. 10, 1995

[30] Foreign Application Priority Data

Jul. 16, 1994 [DE] Germany ............... 44 25 278.1

[51] Int. Cl.$^6$ .................. B01J 23/50; A01N 25/08; A01N 25/34
[52] U.S. Cl. ............... 502/347; 502/344; 424/402; 424/405; 424/409; 523/122
[58] Field of Search .................. 502/340, 344, 502/347, 348; 424/402, 405, 409; 523/122

[56] References Cited

U.S. PATENT DOCUMENTS

| 4,255,341 | 3/1981 | Solomon ............... 260/348.34 |
| 4,677,143 | 6/1987 | Laurin et al. ............... 523/122 |
| 4,849,223 | 7/1989 | Pratt et al. ............... 424/409 |
| 5,147,686 | 9/1992 | Ichimura et al. ............... 427/217 |

FOREIGN PATENT DOCUMENTS

| 190504 | 8/1986 | European Pat. Off. . |
| 0251783 | 1/1988 | European Pat. Off. . |
| 0251873 | 1/1988 | European Pat. Off. . |
| 0270129 | 6/1988 | European Pat. Off. . |
| 0275047 | 7/1988 | European Pat. Off. . |
| 0288063 | 10/1988 | European Pat. Off. . |
| 0322814 | 7/1989 | European Pat. Off. . |
| 427858 | 5/1991 | European Pat. Off. . |
| 4344306 | 6/1994 | Germany . |
| 04/210606 | 12/1990 | Japan . |
| 91/0001 | 1/1991 | WIPO . |

OTHER PUBLICATIONS

Derwent Database WPI, Section Ch, Week 8334, AN 83-744825/34 (1 page abstract).
Chem. Abst., vol. 118 (1993) 75371k.
Journal of Materials Science, vol. 27 (1992) pp. 5027-5030.
Chem. Abst., vol. 115 (1991) 273442k.
Chem. Abstr., vol. 108 (1988) 137657n.

Primary Examiner—Glenn A. Caldarola
Assistant Examiner—Alexander G. Ghyka
Attorney, Agent, or Firm—John H. Shurtleff

[57] ABSTRACT

Mixtures which contain silver with a particle diameter of from 0.001 to 5 µm on a neutral or basic non-zeolite carrier oxide of elements of group IIa, IIIa, IIb, IIIb of the Periodic Table of the Elements, of the lanthanides or mixtures thereof, and a process for preparing these mixtures and antibiotic compositions which comprise these mixtures are described.

12 Claims, No Drawings

MIXTURES CONTAINING FINE METALLIC SILVER PARTICLES ON A NEUTRAL TO BASIC NON-ZEOLITE CARRIER OXIDE

The present invention relates to mixtures which contain silver with a small particle diameter on a neutral or basic non-zeolite carrier oxide, to a process for the preparation thereof and to antibiotic compositions which contain these mixtures.

The growth of microorganisms on carpets and other textiles in occupied rooms is thought to be responsible not only for the dissemination of infectious diseases (especially in hospitals) but also for sick building syndrome, building-related illness and the formation of musty odors.

It has been known for a long time that Ag, Cu and Zn ions have disinfectant properties.

EP-A 275 047, EP-A 322 814, EP-A 288 063 and EP-A 270 129 disclose the use of antibiotic zeolites as additive to plastics and synthetic fibers in order to prevent the growth of microorganisms on the surface thereof. In these cases, silver or another metal ion with antibiotic activity, such as Cu, Zn, Hg, Sn, Pb, Bi, Cd, Cr or Tl is bound in ionic form to ion exchangers. The ion exchangers described were zeolites (A, X, Y and T zeolites), mordenites, sodalites, analcime, chlinoptilolites or erionites as well as amorphous aluminum silicates.

Chem. Abstr. Vol. 118, 75371 k discloses the use of Ag, Cu, Zn, Ni, Pt, Sn, As, Pb, Cd and Cr-containing calcium phosphates, in particular of hydroxyapatites.

$Ag^+$ was bound to clays, especially to montmorillonites, in J. Mater. Sci., 27(18), 5027–30, and to $Na_2Si_2O_5$ in JP 04210606. $AgNO_3$ on $SiO_2$ was described in Chem. Abstr. Vol. 115, 273442 k. $AgCl/TiO_2$ in WO-A 91/00011, and AgCl on aluminosilicate in Chem. Abstr. Vol. 108, 137657 n.

It is particularly important for use in textile fibers that the silver is not leached out on washing and does not discolor on exposure to sunlight. However, ionically bound silver is precipitated as black AgO by alkalis, which leads to discoloration of the products. Colloidal metallic silver likewise has bactericidal properties (Kirk-Othmer, Encyclopedia of Chemical Technology, 1979, 805 to 807) but an intrinsically dark color so that it is unsuitable for doping light-colored fibers (especially carpets).

It is an object of the present invention to remedy the abovementioned disadvantages.

We have found that this object is achieved by novel mixtures which contain silver with a particle diameter of from 0.001 to 5 μm on a neutral or basic non-zeolite carrier oxide of elements of group IIa, IIIa, IIb, IIIb of the Periodic Table of the Elements, of the lanthanides or mixtures thereof, and a process for preparing these mixtures by impregnating the neutral or basic non-zeolite carrier oxides with a silver nitrate or silver acetate solution, drying at from 20° to 200° C. and calcining at from 200° to 600° C. We have furthermore found antibiotic compositions which comprise these mixtures, and antibiotic compositions containing from 0.05 to 80% by weight of a mixture as claimed in claim 1 and from 99.95 to 20% by weight of a resin selected from the group consisting of polyethylene, polypropylene, polyvinyl chloride, ABS resin, polyesters, polyvinyl chlorides, polyamides, polystyrene, polyacetals, polyvinyl alcohol, polycarbonate, acrylic resins, fluorinated plastics, polyurethanes, phenol resins, urea resins, melamine resins, unsaturated polyester resins, epoxy resins, viscose rayon, cuprammonium rayon, acetates, triacetates, vinylidene, natural or synthetic rubbers.

The mixtures according to the invention contain silver in amounts of, as a rule, from 0.001 to 30% by weight, preferably 0.01 to 10% by weight, particularly preferably from 0.1 to 5% by weight, with a particle diameter of from 0.001 to 5 μm, preferably 0.01 to 2 μm, particularly preferably 0.1 to 1.5 μm, on a neutral or basic non-zeolite carrier oxide of the elements of group IIa, IIIa, IIb, IIIb of the Periodic Table of the Elements such as magnesium, calcium, strontium, barium, boron, aluminum, gallium, indium, zinc, scandium, yttrium and lanthanum, preferably magnesium, aluminum, gallium, zinc and lanthanum, and cerium or mixtures thereof. Magnesium and zinc are particularly preferred, especially magnesium. The mixtures may additionally contain from 0.01 to 5% by weight, preferably 0.05 to 3% by weight, particularly preferably 0.1 to 2% by weight, of one or more elements of group VIII of the Periodic Table of the Elements.

The particle diameter of the carrier oxide can vary within wide limits but is, as a rule, from 0.01 to 5000 μm, preferably 0.1 to 1000 μm, particularly preferably 1 to 100 μm, especially 1 to 100 μm, with the ratio of the particle diameter of the carrier oxide to the silver being, as a rule, from 3:1 to 10,000:1, preferably 5:1 to 500:1, particularly preferably 10:1 to 100:1.

We have found, surprisingly, that fine-particle Ag clusters on carriers are substantially colorless or gray and have very good bactericidal properties. In addition, they are stable to the action of alkalis. Fine-particle Ag/carrier powders can be incorporated in a conventional way, with or without a dispersing auxiliary, in plastics, especially in synthetic fibers, and retain their bactericidal action therein.

The metallic silver can be applied by the conventional methods for catalyst preparation. These include impregnation with a silver salt (eg. nitrate, acetate) or a silver complex (eg. $Ag(NH_3)_2OH$), followed by thermal decomposition above 200° C. or a chemical reduction with hydrogen or with an organic compound (eg. formaldehyde). Alternatively, the silver can also be deposited by chemical reduction from the liquid phase or be deposited in vacuo.

In order to obtain products which have as light (or neutral) a color as possible, the silver particles should be smaller than 2 μm, which is favored in particular by the use of basic carriers. It is possible to add to the silver another element (eg. Pd) to enhance the antibiotic effect.

EXAMPLES

Example 1

50 g of $\alpha\text{-}Al_2O_3$ were stirred with a solution of 3.9 g of $AgNO_3$ in 100 ml of water at room temperature for one hour, then evaporated, dried under $N_2$ at 110° C. for 5 h and calcined in $N_2$ at 550° C. for 3 h. The resulting product was pale gray.

Example 2

50 g MgO were stirred with a solution of 3.9 g of $AgNO_3$ in 180 ml of water at room temperature for one hour, then evaporated, dried under $N_2$ at 110° C. for 5 h and calcined in $N_2$ at 550° C. for 3 h. The resulting product was white and did not become dark after addition of 1N NaOH. Only on addition of an $Na_2S$ solution did dark discoloration occur. Examination under the electron microscope showed silver metal particles with a diameter <2 μm on MgO.

Example 3

50 g of $La_2O_3$ were stirred with a solution of 3.9 g of $AgNO_3$ in 100 ml of water at room temperature for one hour, then evaporated, dried under $N_2$ at 110° C. for 5 h and calcined in $N_2$ at 300° C. for 3 h. The resulting product was gray.

Example 4

50 g of ZnO were stirred with a solution of 3.9 g of $AgNO_3$ in 300 ml of water at room temperature for one hour, then evaporated, dried under $N_2$ at 110° C. for 5 h and calcined in $N_2$ at 300° C. for 3 h. The resulting product was pale gray.

Example 5

50 g of $CeO_2$ were stirred with a solution of 3.9 g of $AgNO_3$ in 100 ml of water at room temperature for one hour, then evaporated, dried under N2 at 110° C. for 5 h and calcined in $N_2$ at 300° C. for 3 h. The resulting product was pale gray.

Example 6

50 g of $Ga_2O_3$ were stirred with a solution of 3.9 g of $AgNO_3$ in 100 ml of water at room temperature for one hour, then evaporated, dried under $N_2$ at 110° C. for 5 h and calcined in $N_2$ at 500° C. for 3 h. The resulting product was gray.

Example 7

50 g of $TiO_2$ were stirred with a solution of 3.9 g of $AgNO_3$ in 300 ml of water at room temperature for one hour, then evaporated, dried under $N_2$ at 110° C. for 5 h and calcined in $N_2$ at 500° C. for 3 h. The resulting product was gray and became violet under daylight.

The bactericidal effect was tested by AATCC test method 147-1988 (Antibacterial Activity Assessment of Textile Materials: Parallel Streak Method). The limiting concentration at which the growth of *Klebsiella pneumoniae*, *Pseudomonas aeruginosa* and *Staphylococcus aureus* is suppressed was determined on an agar plate.

Example 8

Test organism *Klebsiella pneumoniae*

−=no growth
+=slight growth
++=growth

| | | Concentration in ppm | | | | |
|---|---|---|---|---|---|---|
| No. | Product | 10000 | 5000 | 2500 | 1000 | 500 |
| 1 | $Ag/Al_2O_3$ | − | − | + | ++ | ++ |
| 2 | Ag/MgO | − | − | − | − | + |
| 3 | $Ag/La_2O_3$ | − | − | + | ++ | ++ |
| 4 | Ag/ZnO | − | − | − | + | + |
| 5 | $Ag/CeO_2$ | − | − | − | ++ | ++ |
| 6 | $Ag/Ga_2O_3$ | − | + | ++ | ++ | ++ |
| 7 | $Ag/TiO_2$ | − | − | − | + | ++ |

Example 9

Test organism *Pseudomonas aeruginosa*

−=no growth
+=slight growth
++=growth

| | | Concentration in ppm | | | | |
|---|---|---|---|---|---|---|
| No. | Product | 10000 | 5000 | 2500 | 1000 | 500 |
| 1 | $Ag/Al_2O_3$ | − | − | ++ | ++ | ++ |
| 2 | Ag/MgO | − | − | − | − | + |
| 3 | $Ag/La_2O_3$ | − | − | − | ++ | ++ |
| 4 | Ag/ZnO | − | + | ++ | ++ | ++ |
| 5 | $Ag/CeO_2$ | − | − | ++ | ++ | ++ |
| 6 | $Ag/Ga_2O_3$ | − | + | ++ | ++ | ++ |
| 7 | $Ag/TiO_2$ | − | − | − | + | ++ |

Example 10

Test organism *Staphylococcus aureus*

−=no growth
+=slight growth
++=growth

| | | Concentration in ppm | | | | |
|---|---|---|---|---|---|---|
| No. | Product | 10000 | 5000 | 2500 | 1000 | 500 |
| 1 | $Ag/Al_2O_3$ | − | + | + | ++ | ++ |
| 2 | Ag/MgO | − | − | − | − | + |
| 3 | $Ag/La_2O_3$ | − | − | + | ++ | ++ |
| 4 | Ag/ZnO | − | − | − | + | + |
| 5 | $Ag/CeO_2$ | − | − | + | ++ | ++ |
| 6 | $Ag/Ga_2O_3$ | − | + | ++ | ++ | ++ |
| 7 | $Ag/TiO_2$ | − | − | − | + | ++ |

We claim:

1. A mixture consisting essentially of metallic silver with a particle diameter of 0.001 to 5 μm applied to a neutral or basic non-zeolite carrier which is an oxide of an element selected from the group consisting of zinc and the element of Group IIa of the Periodic Table of Elements, and mixtures thereof.

2. A mixture as claimed in claim 1, wherein the carrier is a neutral or basic oxide of at least one element selected from the group consisting of zinc, magnesium and calcium.

3. A mixture as claimed in claim 1, wherein the carrier is a basic oxide of at least one element selected from the group consisting of magnesium and calcium.

4. A mixture as claimed in claim 1, wherein the carrier is magnesium oxide.

5. A mixture as claimed in claim 1, wherein the silver has a particle diameter of from 0.01 to 2 μm and is present in the mixture in an amount of from 0.001 to 30% by weight.

6. A mixture as claimed in claim 5, wherein the oxide carrier has a particle diameter of from 0.1 to 1000 μm with the ratio of its particle diameter to that of the silver being from about 5:1 to 500:1.

7. A mixture a claimed in claim 6, wherein the oxide carrier is magnesium oxide, calcium oxide or mixtures thereof.

8. A mixture as claimed in claim 1, wherein said metallic silver has been applied to the oxide carrier by first impregnating the oxide with a silver compound selected from the group consisting of silver nitrate, silver acetate and a silver complex with ammonium hydroxide, then drying at from 20° to 110° C. and calcining in $N_2$ at a temperature of from 150° to 600° C.

9. A fiber-forming textile composition with antibiotic properties comprising a melt-spinnable polyamide resin containing from 0.05 to 80% by weight of a mixture consisting essentially of metallic silver with a particle diameter of 0.001 to 5 μm applied to a neutral or basic non-zeolite carrier which is an oxide of an element selected from the group consisting of zinc and the elements of Group IIa of the Periodic Table of Elements, and mixtures thereof.

10. A composition as claimed in claim 9, wherein said oxide carrier is a basic oxide selected from the group consisting of magnesium oxide, calcium oxide and mixtures thereof.

11. A composition as claimed in claim 9, wherein the silver has a particle diameter of from 0.001 to 2 μm and is present in the mixture in an amount of from 0.001 to 30% by weight.

12. A composition as claimed in claim 10, wherein the silver has a particle diameter of from 0.01 to 1.5 μm and is present in the mixture in an amount of from 0.05 to 3% by weight.

* * * * *